United States Patent
Jaunky et al.

(10) Patent No.: US 7,501,536 B2
(45) Date of Patent: Mar. 10, 2009

(54) ODORANT COMPOUNDS, SYNTHESIS METHOD, AND USES OF SAID COMPOUNDS

(75) Inventors: Piotr Jaunky, Grasse (FR); Jean Mane, Grasse (FR); Martin Schroeder, Ashford (GB)

(73) Assignee: V. Mane Fils, Bar sur Loup (FR)

( * ) Notice: Subject to any disclaimer, the term of this patent is extended or adjusted under 35 U.S.C. 154(b) by 0 days.

(21) Appl. No.: 11/795,496

(22) PCT Filed: Jan. 13, 2006

(86) PCT No.: PCT/FR2006/000080

§ 371 (c)(1),
(2), (4) Date: Aug. 6, 2007

(87) PCT Pub. No.: WO2006/077305

PCT Pub. Date: Jul. 27, 2006

(65) Prior Publication Data

US 2008/0118443 A1 May 22, 2008

(30) Foreign Application Priority Data

Jan. 19, 2005 (FR) .................................. 05 00551

(51) Int. Cl.
*C07C 41/00* (2006.01)
*C07C 31/00* (2006.01)
*C07C 45/00* (2006.01)
*A61K 8/18* (2006.01)

(52) U.S. Cl. ........................ 560/129; 560/205; 568/449; 568/671; 568/687; 568/840; 512/27; 424/49

(58) Field of Classification Search ........................ None
See application file for complete search history.

(56) References Cited

U.S. PATENT DOCUMENTS 3,920,752 A 11/1975 Lamparsky et al.
3,959,396 A 5/1976 Ochsner et al.

FOREIGN PATENT DOCUMENTS

JP 5-202378 A 8/1993
WO 01/27234 A 4/2001

*Primary Examiner*—Sikarl A Witherspoon
(74) *Attorney, Agent, or Firm*—Young & Thompson

(57) ABSTRACT

A compound of general formula (I) with or without the double bond illustrated by the dotted line. In formula (I), X is a CHO, CH2OH, CH2OC(O)R or CH(OR)2 group, and R represents a linear or branched C1-C5 alkyl or alkenyl chain. The synthesis method for the compound, and especially the 6,8-dimethyl-non-7-enal (1) prepared by the hydroformylation of the 5,7-dimethyl-octa-1,6-diene is also disclosed, as well as compositions containing the compounds of formula (I). Due to the odorant properties thereof, the compounds are highly useful in perfumery, especially for cosmetic products and household products.

20 Claims, No Drawings

ODORANT COMPOUNDS, SYNTHESIS METHOD, AND USES OF SAID COMPOUNDS

The present invention relates to novel odorous compounds which can be used in perfumery. The invention relates in particular to novel aldehydes, to their corresponding alcohols and ethers, to their process of synthesis and to their uses in perfumery.

The term "perfumery" is used here to denote not only perfumery in the usual sense of the term but also the other fields in which the odor of products is important. Perfumery compositions in the usual sense of the term may be involved, such as fragrance bases, perfume concentrates, eaux de Cologne, toilet waters, fragrances and similar products; topical compositions, in particular cosmetics, such as creams for the face and body, talcum powders, hair oils, shampoos, hair lotions, bath salts and oils, shower and bath gels, toilet soaps, antiperspirants and deodorants for the body, shaving lotions and creams, soaps, creams, toothpastes, mouthwashes, pomades and similar products; and cleaning products, such as softeners, detergents, washing powders, air fresheners and similar products.

Aldehydes represent one of the main families of odorous molecules used in perfumery. In this family, the aldehydes having between 8 and 12 carbon atoms play an important role. Terpene aldehydes, which have floral odors, are included among these aldehydes. Linear aldehydes derived from fatty acids, which have fresh notes typical of fruit of the citrus family, are also included.

Aldehydes combining both these types of odor currently do not exist. In any case, the need remains for novel odorous agents in order to extend the range of the notes which can be introduced into a composition and the options available for adding these notes.

A subject matter of the present invention is the novel compounds represented by the following general formula (I):

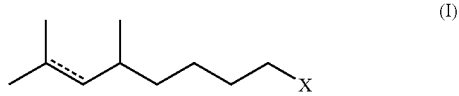

in which X is a CHO, $CH_2OH$, $CH_2OC(O)R$ or $CH(OR)_2$ group and R represents a linear or branched $C_1$-$C_5$ alkyl or alkenyl chain, and the bond given as a dotted line is present or absent.

The compound of formula (I) can be present in the form of an isomer or of a mixture of isomers, in particular of an enantiomer or a mixture of enantiomers, or of a racemic mixture, or of a diastereoisomer or of a mixture of diastereoisomers.

In particular, the present invention relates to a compound of formula (I) in which the bond given as a dotted line is present and X represents a —CHO group; this novel aldehyde, of formula (1) below, is 6,8-dimethylnon-7-enal (1). The invention also relates to the process of synthesis and to the use of this compound (1) as odorous agent by virtue of its fresh, orange peel and herbaceous notes with coriander leaf accents.

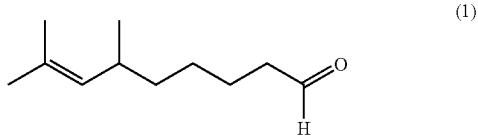

(1)

Among the enantiomers of the compound (1), which are all targeted by the present invention, a particularly preferred compound is 6(R),8-dimethylnon-7-enal.

The compound of formula (1) is prepared, according to the invention, by hydroformylation of 5,7-dimethylocta-1,6-diene and is represented by the following scheme:

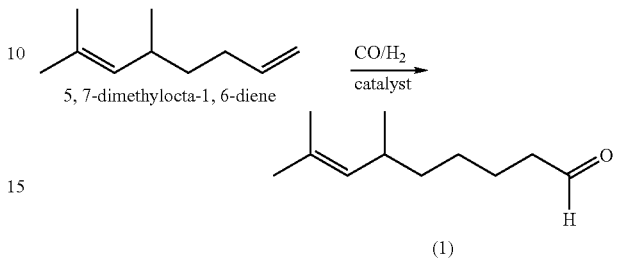

Hydroformylation is a well known reaction. A person skilled in the art today has a choice between several catalysts which allow him to introduce an aldehyde functional group into an unsaturated molecule and will thus be in a position to choose the catalyst or system of catalysts and to determine the reaction conditions.

Use may be made, as an example, in the process according to the invention, of a system of catalysts, bis($\eta^4$-1,5-cyclooctadiene)di($\mu$-methoxy)dirhodium(I) (A) and diphenylphosphino-1,8-dimethyl-9,9-xanthene (Xantphos) (B), described by Claudia Foca, Humberto J. V. Barros, Eduardo N. dos Santos, Elena V. Gusevskaya and J. C. Bayon, New Journal of Chemistry (2003), 27(3), 533-539. This system of catalysts is advantageous as a result of the ease of the synthesis thereof and of the use thereof. It forms, in the presence of carbon monoxide and hydrogen, an active complex [RhH(diphosphine)$CO_2$] which reacts with the alkene present. Other diphosphines can also be used to form a diphosphine-rhodium complex, as shown, for example, by Immaculada del Rio, Wim G. J. de Lange, Piet W. N. M. van Leeuwen and Carmen Claver, Journal of the Chemical Society, Dalton Transactions (2001), (8), 1293-1300, or by Montserrat Dieguez, Mariette M. Pereira, Anna M. Masdeu-Bulto, Carmen Claver and J. Charles Bayon, Journal of Molecular Catalysis A: Chemical (1999), 143-(1-3), 111-112.

Of course, the rhodium catalyst [Rh(OMe)(COD)$_2$] (A) can also be substituted by catalysts such as [Rh(acac)(CO)$_2$] or [Rh(OAc)(COD)]$_2$, for example, as described by Piet W. N. M. van Leeuwen and Carmen Claver (editors) in "Rhodium Catalysed Hydroformylation", Catalysis by Metal Complexes, Vol. 22, Kluwer Academic Publishers, Dordrecht, The Netherlands, (2000), ISBN 0-7923-6551-8.

According to one embodiment of the process according to the invention, use is thus made, as hydroformylation catalyst, of the system of catalysts bis($\eta^4$-1,5-cyclooctadiene)di($\mu$-methoxy)dirhodium(I) (A) and diphenylphosphino-1,8-dimethyl-9,9-xanthene (Xantphos) (B). The reaction can then be carried out using from $1 \times 10^{-3}$ to $1 \times 10^{-4}$ equivalent, preferably from $2 \times 10^{-4}$ to $5 \times 10^{-4}$ equivalent, of catalyst with respect to the starting alkene.

According to this embodiment, the reaction is carried out in an autoclave into which the 5,7-dimethylocta-1,6-diene, thoroughly degassed, is charged under nitrogen. The catalyst (A) and the cocatalyst (B) are also added under nitrogen. The reaction can be carried out using from $1 \times 10^{-3}$ to $1 \times 10^{-4}$ equivalent, preferably from $2 \times 10^{-4}$ to $5 \times 10^{-4}$ equivalent, of catalyst with respect to the alkene. The autoclave is subsequently closed and purged several times with an equimolar mixture of carbon monoxide and hydrogen. The internal pressure of the autoclave can be adjusted to a value from approximately 5×10³ to 8×10⁴ HPa, preferably from 3×10⁴ to 6×10⁴ HPa, and the reaction medium is heated, in particular to a temperature from approximately 60 to 120° C., preferably 100° C. The conversion is monitored by gas chromatography and the product is recovered after approximately 12 hours and directly distilled, providing the 6,8-dimethylnon-7-enal (1).

The present invention relates to another novel compound, 6,8-dimethylnon-7-anal (1'), that is to say the compound of formula (I) where the bond given as a dotted line is absent and X represents a —CHO group, to its process of synthesis and to its use as odorous agent.

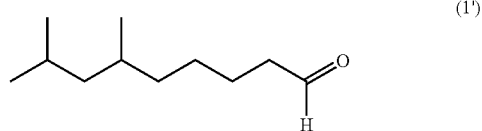

(1')

The present invention also relates to the acyclic or cyclic acetals of the compounds (1) and (1'), that is to say the compounds of formula (I) where X represents a —CH(OR)₂ group where R represents a linear or branched $C_1$-$C_5$ alkyl or alkenyl chain and the bond given as a dotted line is present or absent, to their process of synthesis and to their use as odorous agents.

The present invention also relates to the unsaturated alcohol (2) and the saturated alcohol (2') derived from (1) and (1') respectively, that is to say the compounds of formula (I) where X represents a —CH₂OH group and the bond given as a dotted line is present (2) or absent (2'), to their process of synthesis and to their use as odorous agents:

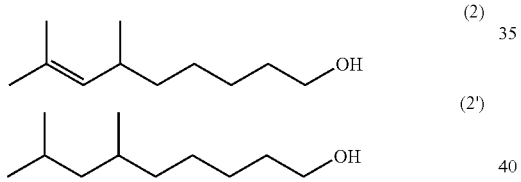

The alcohols (2) and (2') of the present invention can be easily prepared by reduction of the compounds of formula (1) under conditions well known to a person skilled in the art. In a specific embodiment of the invention, the unsaturated alcohol (2) is obtained by selective reduction of the aldehyde functional group (1) by a reducing agent, such as sodium borohydride (NaBH₄), and the saturated alcohol (2') is synthesized by reduction of the aldehyde functional group and of the C—C double bond of the compound (1) by hydrogen in the presence of a catalyst, such as palladium-on-charcoal.

The saturated aldehyde (1') of the present invention can be prepared by oxidation of (2') according to methods well known to a person skilled in the art, such as, for example, by Corey's reagent (CrO₃/pyridine/HCl).

The present invention also relates to the esters (3) and (3') derived from the alcohols (2) and (2') respectively, that is to say the compounds of formula (I) where X represents a —CH₂OC(O)R group where R represents a linear or branched $C_1$-$C_5$ alkyl or alkenyl chain and the bond given as a dotted line is present (3) or absent (3'), in particular the acetate, propionate, butyrate, isobutyrate, pentanoate, 2-methylbutyrate, 3-methylbutyrate, hexanoate, 2-methylpentanoate, 3-methylpentanoate, 4-methylpentanoate, 2,2-dimethylbutyrate, 2,3-dimethylbutyrate and 3,3-dimethylbutyrate, 2-butenoate, 2-methyl-2-butenoate or 3-hexenoate of 6,8-dimethylnon-7-enol (2) and of 6,8-dimethylnon-7-anol (2').

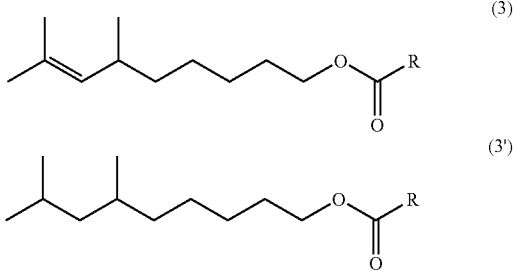

The invention also relates to the process for the synthesis of these esters and to their use as odorous agents.

The esters (3) and (3') of the present invention can be respectively prepared from (2) and (2'), in particular by esterification of the appropriate linear or branched $C_1$-$C_5$ acids or acyl chlorides, according to conditions well known to a person skilled in the art.

A scheme for the synthesis of the compounds of the invention is given below, as nonlimiting example:

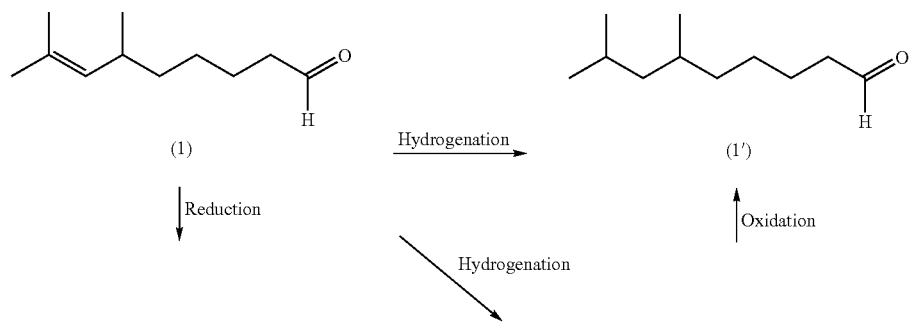

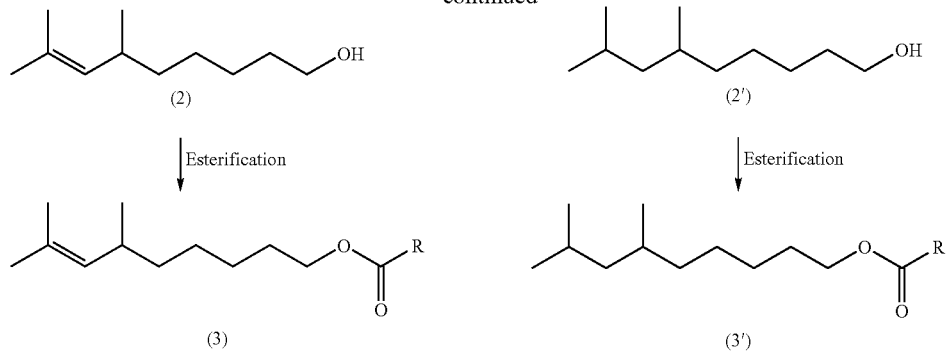

R=linear or branched $C_1$-$C_5$ alkyl or alkenyl chain

Due to their odorous properties, the compounds of formula (I) have a great variety of uses in perfumery, within the meaning explained in detail above, in particular and without implied limitation in cosmetics and for cleaning products.

Another subject matter of the invention is the use of at least one compound of formula (I) according to the invention as odorous agent, as odor-masking agent or as odor-neutralizing agent, alone or as a mixture with one or more other odorous compounds known to a person skilled in the art which a person skilled in the art is in a position to choose according to the effect desired. The additional odorous agent or agents can be compounds of formula (I) or other odorous agents known to a person skilled in the art.

Another subject matter of the invention is the compositions comprising a base product and an effective amount of one or more compounds of formula (I) according to the invention.

It can be a composition which is itself odorous or a composition in which the odorous agent is used to mask or neutralize certain odors.

The base product will be easily determined by a person skilled in the art according to the composition envisaged and thus the use envisaged, the usual components for which, such as solvent(s) and/or adjuvant(s), are well known.

The effective amount of the compounds of formula (I) according to the invention incorporated in the composition will vary according to the nature of the composition, the odorous effect desired and the nature of the other odorous or nonodorous compounds possibly present and can be easily determined by a person skilled in the art, it being known that it can vary within a very broad range from 0.1 to 99% by weight, in particular 0.1 to 50% by weight, in particular 0.1 to 30% by weight.

The compounds of formula (I) according to the invention can be used as is or they can be incorporated in or on an inert support material or a support material which can comprise other active ingredients of the finished composition. A great variety of support materials can be employed, including, for example, polar solvents, oils, fats, finely divided solids, cyclodextrins, maltodextrins, gums, resins and any other support material known for such compositions.

Another subject matter of the invention is thus the use of the compounds of formula (I) in the preparation of an odorous composition or of an odorous article in the applications described above, in particular in perfumery or in cosmetics, for example for shampoos, soaps, and in cleaning products, such as softeners or washing powders.

The invention relates in particular to a perfumery composition, especially a fragrance base or a perfume concentrate, an eau de Cologne, a toilet water or a fragrance, comprising at least one compound of formula (I) or a composition comprising at least one compound of formula (I).

The invention also relates in particular to a cosmetic composition, in particular a cream for the face and body, talcum powder, oil for the hair or for the body, shampoo, hair lotion, bath soap, bath oil, shower gel, bath gel, toilet soap, antiperspirant for the body, deodorant for the body, shaving lotion or cream, shaving soap, cream, toothpaste, mouthwash or pomade, comprising at least one compound of formula (I) or at least one composition comprising at least one compound of formula (I). Another subject matter of the invention is a preventative or nonpreventative cosmetic treatment or care method employing at least one compound of formula (I) or at least one composition comprising at least one compound of formula (I).

The invention also relates to a cleaning product, in particular softener, detergent, washing powder or air freshener, comprising at least one compound of formula (I) or at least one composition comprising at least one compound of formula (I).

The following examples further illustrate the novel odorous compounds, their process of synthesis, their advantage and their uses. These examples are presented only with an illustrative purpose and may not be regarded as limitations on the invention.

EXAMPLE 1

Synthesis of 6,8-dimethylnon-7-enal (1)

138.0 g (1.00 mol) of degassed 5,7-dimethylocta-1,6-diene are charged under nitrogen to an autoclave in which a glass container has been placed. 232 mg (0.48 mmol) of bis($\eta^4$-1,5-cyclooctadiene)di(μ-methoxy)dirhodium(I) (A) and 836 mg (1.44 mmol) of diphenylphosphino-1,8-dimethyl-9,9-xanthene (B) are added. The autoclave is closed and purged three times with an equimolar mixture of carbon monoxide and hydrogen. The internal pressure is adjusted to $3 \times 10^4$ HPa. Heating is carried out slowly to 100° C., taking the exothermicity of the reaction into consideration, without exceeding a bulk temperature of 120° C. The reaction medium is heated under these conditions for 12 hours. Cooling is carried out to ambient temperature and then the product is transferred into a distillation apparatus. After having recovered the 5,7-dimethylocta-1,6-diene (41.6 g, B.p.: 35° C./60 HPa), 88.2 g (0.48 mol) of 6,8-dimethylnon-7-enal (1), B.p.: 48° C./3.5 HPa, are obtained. The yield is 48%. The analyses of the infrared, NMR and mass spectra correspond to the structure of the aldehyde (1).

EXAMPLE 2

Synthesis of 6,8-dimethylnon-7-enol (2)

18 g (0.11 mol) of 6,8-dimethylnon-7-enal (1) and 96.0 g of ethanol are placed in a 500 ml round-bottomed flask equipped with a thermometer. Cooling is carried out to 5° C. and 2.0 g of sodium borohydride are added in small portions without exceeding a bulk temperature of 10° C. The mixture is stirred at ambient temperature for 16 hours. Cooling is carried out to 5° C. and 20.0 g (1.36 mol) of acetone are added dropwise to destroy the excess reducing agent without exceeding a bulk temperature of 10° C. The reaction medium is acidified with 20.0 g of 10% hydrochloric acid without exceeding a bulk temperature of 10° C. 40 g of water are also added, followed by 70 g of toluene, with vigorous stirring. The phases are separated and the organic phase is washed once with 50 g of saturated aqueous $NaHCO_3$ solution and twice with 50 g of water. The organic phase is dried and filtered, and the toluene is evaporated at reduced pressure. After distillation, 13.4 g (0.08 mol) of (B.p.: 105° C./10 torr) are obtained. The yield is 72.7%. The analyses of the infrared, NMR and mass spectra correspond to the expected alcohol.

EXAMPLE 3

6,8-Dimethylnon-7-enol acetate 13 g (76 mmol) of 6,8-dimethylnon-7-enol (2), 10.8 g (107 mmol) of triethylamine and 200 ml of t-butyl methyl ether (MTBE) are placed in a 500 ml round-bottomed flask equipped with a thermometer and with a dropping funnel. Cooling is carried out to 5° C. and 8.4 g (107 mmol) of acetylchloride diluted in 20 ml of MTBE are added without exceeding a bulk temperature of 10° C. The mixture is stirred at ambient temperature for 14 hours. Cooling is carried out at 5° C. and neutralization is carried out with 100 ml of a 10% hydrochloric acid solution. The phases are separated and the organic phase is washed once with 100 ml of saturated aqueous $NaHCO_3$ solution and then with aqueous saline solution to neutrality. The organic phase is dried and filtered, and the solvent is evaporated under reduced pressure. The acetate is purified by a distillation under reduced pressure (B.p.: 58° C./0.4 torr). The yield is 76%.

EXAMPLE 4

6,8-Dimethylnon-7-enol propionate

It is obtained according to example 3 using propionyl chloride. The yield is 71% (B.p.: 70° C./0.6 torr).

EXAMPLE 5

Olfactory Evaluation of the Pure Compound (1)

In a first step, the odorous characteristics of the pure compound (1) were evaluated by a panel. The evaluation panel was composed of several professionals who quantitatively evaluate the compound. The compound (1) was described as fresh, orange peel and herbaceous with coriander leaf accents. If the aldehyde (1) is diluted to 1% in propylene glycol, its fruity notes become dominant and a melon note may be perceived.

EXAMPLE 6

Olfactory Evaluation of the Compound (1) in Two Compositions

Subsequently, two fragrance compositions were created in which the olfactory impact of the compound (1) was examined. These fragrance compositions can be used for topical cosmetic products of shampoo, shower gel or cream type, and the like.

In each case, the evaluations of the olfactory impact were carried out at $t_0$, $t_{+48h}$ and $t_{+168h}$ in order to evaluate the top, middle and base notes of the composition comprising the compound (1) (test 2), in comparison with a composition not comprising the compound (test 1).

| Composition No. 1 | | |
|---|---|---|
| Component | Test 1 (% by weight) | Test 2 (% by weight) |
| Isoamyl acetate | 1.0 | 1.0 |
| Geranyl acetate | 2.5 | 2.5 |
| Hexyl acetate[1] | 1.5 | 1.5 |
| Styrallyl acetate | 0.5 | 0.5 |
| Vertenyl acetate[2] | 2.0 | 2.0 |
| α-Hexylcinnamaldehyde | 10.0 | 10.0 |
| γ-Undecalactone | 4.0 | 4.0 |
| Allyl caproate[3] | 1.0 | 1.0 |
| Cyclamen aldehyde Extra[4] | 1.0 | 1.0 |
| Cyclogalbanate[5] | 0.5 | 0.5 |
| Galaxolide[6] | 14.0 | 14.0 |
| β-Ionone | 4.0 | 4.0 |
| Ethyl 2-methylbutyrate | 1.5 | 1.5 |
| Terpineol | 8.0 | 8.0 |
| Triplal[7] | 0.5 | 0.5 |
| Verdox[8] | 20.0 | 20.0 |
| Verdyl propionate[9] | 2.5 | 2.5 |
| Benzaldehyde | 2.5 | 2.5 |
| Ethyl butyrate[1] | 2.5 | 2.5 |
| Folione[10][11] | 3.5 | 3.5 |
| 3-cis-Hexenol[1] | 1.5 | 1.5 |
| 6-cis-Nonenol[1] | 3.0 | 3.0 |
| trans-2, cis-6-Nonadienol[12] | 1.5 | 1.5 |
| Ethyl maltol[1] | 2.5 | 2.5 |
| Dipropylene glycol | 10.0 | 9.0 |
| 6,8-Dimethylnon-7-enal[1] | 0.0 | 1.0 |
| Total | 100.0 | 100.0 |

[1]At 10% in dipropylene glycol
[2]4-tert-Butylcyclohexyl acetate; origin: International Flavors and Fragrances, USA.
[3]Origin: V. Mane Fils, France.
[4]3-(4-Isopropylphenyl)-2-methylpropionaldehyde; origin: Givaudan, Switzerland.
[5](Cyclohexyloxy)acetic acid, 2-propenyl ester; origin: Symrise, Germany.
[6]1,1,2,3,3,8-Hexamethyl-1,2,3,5,7,8-hexahydro-6-oxa-cyclopenta[b]naphthalene; origin: International Flavors and Fragrances, USA.
[7]2,4-Dimethylcyclohex-3-enecarbaldehyde; origin: International Flavors and Fragrances, USA.
[8]Acetic acid, 2-(tert-butyl)cyclohexyl ester, origin: International Flavors and Fragrances, USA.
[9]Propionic acid, 3a,4,5,6,7,7a-hexahydro-1H-4,7-methanoinden-5-yl ester; origin: Givaudan, Switzerland.
[10]At 1% in dipropylene glycol.
[11]Methyl 2-octynoate; origin: Givaudan, Switzerland.
[12]At 1% in dipropylene glycol.

| Composition No. 2 | | |
|---|---|---|
| Component | Test 1 (% by weight) | Test 2 (% by weight) |
| Phenylethyl alcohol | 1.0 | 1.0 |
| α-Hexylcinnamaldehyde | 8.0 | 8.0 |
| Canthoxal[1] | 0.5 | 0.5 |
| Citronellol | 2.0 | 2.0 |
| Eugenol[2] | 1.0 | 1.0 |
| Galaxolide[3] | 25.0 | 25.0 |
| γ-Decalactone | 0.3 | 0.3 |
| Methyl dihydrojasmonate[4] | 3.0 | 3.0 |
| Helional[6] | 3.0 | 3.0 |

-continued

Composition No. 2

| Component | Test 1 (% by weight) | Test 2 (% by weight) |
|---|---|---|
| β-Ionone | 0.2 | 0.2 |
| Isoananate[6] | 0.1 | 0.1 |
| ISO E Super[7] | 12.0 | 12.0 |
| Lilial[8] | 11.0 | 11.0 |
| Linalool | 3.0 | 3.0 |
| Lyral[9] | 2.5 | 2.5 |
| Methylionantheme Super[10] | 3.0 | 3.0 |
| Rosafix[11] | 0.1 | 0.1 |
| Amyl salicylate | 4.0 | 4.0 |
| Benzyl salicylate | 4.0 | 4.0 |
| Terpineol | 0.2 | 0.2 |
| Vertenex[12] | 4.0 | 4.0 |
| Adoxal[13] | 0.4 | 0.4 |
| Phenylacetaldehyde[14] | 0.3 | 0.3 |
| 3(Z)-Hexenyl butyrate[15] | 0.6 | 0.6 |
| Damascenone[14)16] | 0.2 | 0.2 |
| Indol[14] | 1.2 | 1.2 |
| Melonal[14)17] | 0.8 | 0.8 |
| Tagette Ess. Egypt[14] | 2.5 | 2.5 |
| Triplal[14)18] | 0.8 | 0.8 |
| Dipropylene glycol | 5.3 | 2.8 |
| 6,8-Dimethylnon-7-enal[14] | 0.0 | 2.5 |
| Total | 100.0 | 100.0 |

[1] 3-(4-Methoxyphenyl)-2-methylpropionaldehyde; origin: International Flavors and Fragrances, USA.
[2] Origin: V. Mane Fils, France.
[3] 1,1,2,3,3,8-Hexamethyl-1,2,3,5,7,8-hexahydro-6-oxa-cyclopenta[b]naphthalene; origin: International Flavors and Fragrances, USA.
[4] [3-Oxo-2-((E)-pentyl)cyclopentyl]acetic acid, methyl ester; origin: Firmenich, Switzerland.
[5] 3-(Benzo[1,3]dioxol-5-yl)-2-methylpropionaldehyde; origin: International Flavors and Fragrances, USA.
[6] Cyclohexyloxyacetic acid, allyl ester; origin: Symrise, Germany.
[7] 1-(2,3,8,8-Tetramethyl-1,2,3,4,5,6,7,8-octahydro-naphth-2-yl)ethanone; origin: International Flavors and Fragrances, USA.
[8] 3-(4-(tert-Butyl)phenyl)-2-methylpropionaldehyde; origin: Givaudan, Switzerland.
[9] 4-(4-Hydroxy-4-methylpentyl)cyclohex-3-enecarbaldehyde, origin: International Flavors and Fragrances, USA.
[10] (E)-3-Methyl-4-(2,6,6-trimethylcyclohex-3-enyl)but-3-en-2-one; origin: International Flavors and Fragrances, USA.
[11] Acetic acid, 2,2,2-trichloro-1-phenylethyl ester; origin: Symrise, Germany.
[12] Acetic acid, 4-(tert-butyl)cyclohexyl ester; origin: International Flavors and Fragrances, USA.
[13] 2,6,10-Trimethylundec-9-enal; origin: Givaudan, Switzerland.
[14] At 10% in dipropylene glycol.
[15] At 1% in dipropylene glycol.
[16] 1-(2,6,6-Trimethyl-1,3-cyclohexadien-1-yl)-2-buten-1-one; origin: Firmenich, Switzerland.
[17] 2,6-Dimethylhept-5-enal; origin: Givaudan, Switzerland.
[18] 2,4-Dimethylcyclohex-3-enecarbaldehyde; origin: International Flavors and Fragrances, USA.

The presence of 6,8-dimethylnon-7-enal (1) in composition No. 1 considerably changes its odor from an apple to a sweet, fleshy and very pleasantly natural green melon.

The 6,8-dimethylnon-7-enal (1) contributes fruity notes, in particular green melon, and the seaside to composition No. 2. It also gives more strength to the top notes.

The loss in intensity with time appears to be fairly linear, without allowing a significant change in odorous characteristic to appear.

The results of these evaluations show, without the slightest doubt, that the compound (1) according to the invention exhibits advantageous olfactory characteristics which will find application in perfumery, in particular in cosmetics and cleaning products and generally in any odorous composition or composition having an odor which it is desired to mask or neutralize.

EXAMPLE 7

Olfactory Evaluation of Compound (2), Pure and in a Composition

An evaluation panel similar to that of example 5 drew up, for the pure compound (2), the following olfactory description: rustic, floral, bergamot, cinnamon.

The olfactory impact of compound (2) was subsequently tested in a synthetic bergamot composition (test 2), in comparison with a composition not comprising the compound (test 1).

|  | Bergamot without 6,8-dimethylnon-7-enol Test 1 | Bergamot with 6,8-dimethylnon-7-enol Test 2 |
|---|---|---|
| Orange terpenes | 270 | 270 |
| Linalyl acetate | 320 | 320 |
| Linalool | 150 | 150 |
| γ-Terpinene | 75 | 75 |
| β-Pinene | 70 | 70 |
| Citral from *Litsea cubeba* | 5 | 5 |
| Orange Brazil ess. | 5 | 5 |
| Geranyl acetate | 5 | 5 |
| Dipropylene glycol | 100 | X |
| 6,8-Dimethylnon-7-enol | X | 100 |

The tests carried out show that the presence of 6,8-dimethylnon-7-enol reinforces the bergamot note and gives strength to the product. Its effect is even more striking after 2 h 00 of evaporation; the bergamot note persists in the middle.

What is claimed is:

1. A compound of general formula (I):

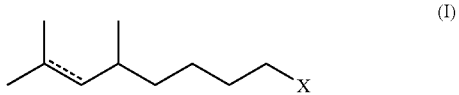

(I)

in which X is a CHO, $CH_2OH$, $CH_2OC(O)R$ or $CH(OR)_2$ group and R represents a linear or branched $C_1$-$C_5$ alkyl or alkenyl chain, and
the bond given as a dotted line is present or absent.

2. The compound as claimed in claim 1, characterized in that it is in the enantiomerically pure form, in particular in the form of the R enantiomer or in the form of the S enantiomer, or in the form of a mixture of enantiomers, in particular of the racemic mixture.

3. The compound as claimed in claim 1, characterized in that it is 6,8-dimethylnon-7-enal (1)

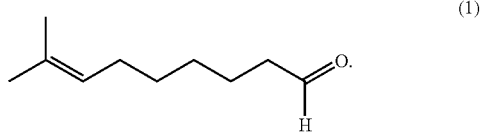

(1)

4. The compound as claimed in claim 1, characterized in that it is 6(R), 8-dimethylnon-7-enal.

5. The compound as claimed in claim 1, characterized in that is 6,8-dimethylnon-7-anal (1')

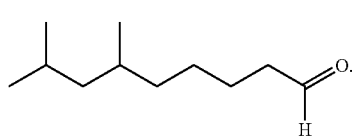

6. The compound as claimed in claim 1, characterized in that it is 6,8-dimethylnon-7-enol (2).

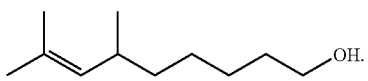

7. The compound as claimed in claim 1, characterized in that it is 6,8-dimethylnon-7-anol (2')

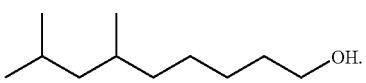

8. The compound as claimed in claim 1, corresponding to the formula (I) in which X represents a —CH(OR)$_2$ group where R represents a linear or branched $C_1$-$C_5$ alkyl or alkenyl chain (it being possible for the —CH(OR)$_2$ group to be cyclic or acyclic) and the bond given as a dotted line is present or absent.

9. The compound as claimed in claim 1, corresponding to the formula (I) in which X represents a —CH$_2$OC(O)R group where R represents a linear or branched $C_1$-$C_5$ alkyl or alkenyl chain and the bond given as a dotted line is present (3) or absent (3')

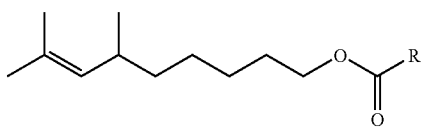

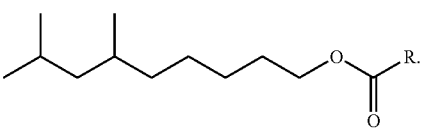

10. The compound as claimed in claim 9, which is an ester derived from the acetate, propionate, butyrate, isobutyrate, pentanoate, 2-methylbutyrate, 3-methylbutyrate, hexanoate, 2-methylpentanoate, 3-methylpentanoate, 4-methylpentanoate, 2,2-dimethylbutyrate, 2,3-dimethylbutyrate and 3,3-dimethylbutyrate, 2-butenoate, 2-methyl-2-butenoate or 3-hexenoate of 6,8-dimethylnon-7-enol (2) and 6,8-dimethylnon-7-anol (2').

11. A process for the preparation of the compound of formula (I):

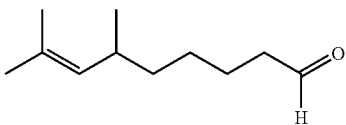

comprising the hydroformylation of 5,7-dimethylocta-1,6-diene.

12. The process as claimed in claim 11, characterized in that use is made of the system of catalysts bis($\eta^4$-1,5-cyclooctadiene)di($\mu$-methoxy)dirhodium(I) and diphenylphosphino-1,8-dimethyl-9,9-xanthene (Xantphos) as catalyst for the hydroformylation.

13. A composition, characterized in that it comprises at least one compound of formula (I) as defined in claim 1 in the form of an isomer or of a mixture of isomers, in particular of an enantiomer or of a mixture of enantiomers, or of a racemic mixture, or of a diastereoisomer or mixture of diastereoisomers.

14. The composition as claimed in claim 13, characterized in that said compound or compounds of formula (I) are incorporated in or on an inert support material or a support material which can comprise other active ingredients, said support being chosen in particular from polar solvents, oils, fats, finely divided solids, cyclodextrins, maltodextrins, gums or resins.

15. A perfumery composition, in particular fragrance base or perfume concentrate, eau de Cologne, toilet water or fragrance, characterized in that it comprises at least one compound as defined in claim 1.

16. A cosmetic composition, in particular a cream for the face and body, talcum powder, oil for the hair or for the body, shampoo, hair lotion, bath salt, bath oil, shower gel, bath gel, toilet soap, antiperspirant for the body, deodorant for the body, shaving lotion or cream, shaving soap, cream, toothpaste, mouthwash or pomade, characterized in that it comprises at least one compound as defined in claim 1.

17. A cleaning product, in particular softener, detergent, washing powder or air freshener, characterized in that it comprises at least one compound as defined in claim 1.

18. The compound as claimed in claim 2, characterized in that it is 6,8-dimethylnon-7-enal (1)

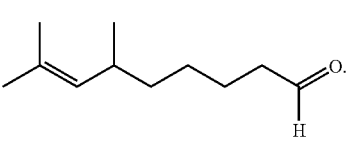

19. The compound as claimed in claim 2, characterized in that it is 6(R), 8-dimethylnon-7-enal.

20. The compound as claimed in claim 2, characterized in that is 6,8-dimethylnon-7-anal (1').

* * * * *